United States Patent [19]

Kitajima et al.

[11] Patent Number: 5,045,286

[45] Date of Patent: Sep. 3, 1991

[54] DEVICE FOR ASPIRATING A FIXED QUANTITY OF LIQUID

[75] Inventors: Masaichi Kitajima, Akigawa; Takayuki Aihara; Hajime Sakuma, both of Hachioji, all of Japan

[73] Assignee: Olympus Optical Co., Ltd., Tokyo, Japan

[21] Appl. No.: 311,463

[22] Filed: Feb. 15, 1989

[30] Foreign Application Priority Data

Feb. 25, 1988 [JP] Japan .................................. 63-40604
Mar. 24, 1988 [JP] Japan .................................. 63-70731

[51] Int. Cl.⁵ .......................... B01L 3/02; G01F 23/24
[52] U.S. Cl. ...................................... 422/100; 436/54; 73/864.11; 73/864.24; 73/304 R; 73/304 C; 141/95; 141/130
[58] Field of Search ............... 422/100, 63; 73/864.02, 73/864.11, 864.13, 864.18, 864.21, 864.24, 304 R, 304 C; 439/428; 436/54; 141/95, 96, 130

[56] References Cited

U.S. PATENT DOCUMENTS

| | | | |
|---|---|---|---|
| 3,635,094 | 1/1972 | Oberli | 73/863.01 |
| 3,992,073 | 11/1976 | Buchoff et al. | 439/482 X |
| 4,276,260 | 6/1981 | Drbal | 422/100 |
| 4,399,711 | 8/1983 | Klein | 422/64 X |
| 4,451,433 | 5/1984 | Yamashita et al. | 436/54 X |
| 4,478,094 | 10/1984 | Salomma et al. | 422/65 X |
| 4,528,158 | 7/1985 | Gilles et al. | 422/65 X |
| 4,794,085 | 12/1988 | Jessop et al. | 422/64 X |
| 4,897,244 | 1/1990 | Wallace et al. | 73/864.24 X |

FOREIGN PATENT DOCUMENTS

| | | |
|---|---|---|
| 0052006A1 | 5/1982 | European Pat. Off. |
| 0250671A1 | 1/1988 | European Pat. Off. |
| 62-247261 | 10/1987 | Japan |

*Primary Examiner*—David L. Lacey
*Assistant Examiner*—Jeffrey R. Snay
*Attorney, Agent, or Firm*—Frishauf, Holtz, Goodman & Woodward

[57] ABSTRACT

A device for injecting a fixed quantity of sample liquid is provided with a unit for aspirating and injecting sample liquid. The sample aspirating and injection unit has a nozzle connecting portion. The liquid injection device is provided with an injection nozzle attached to and detachable from the nozzle connecting portion of the sample aspirating and injecting unit and electrodes are attached to the injection nozzle. Conductive members which are electrically connected to the electrodes of the injection nozzle are attached to the nozzle connecting portion of the sample aspirating and injecting unit, and a detecting unit which cooperates with the electrodes to detect the surface level of sample liquid is connected to the conductive members.

8 Claims, 5 Drawing Sheets

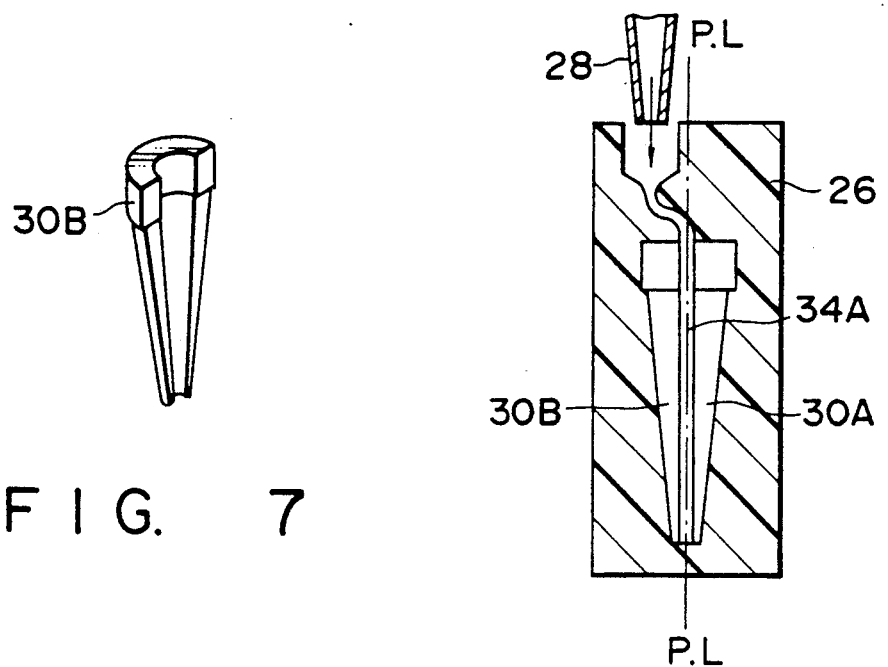
FIG. 7
FIG. 8
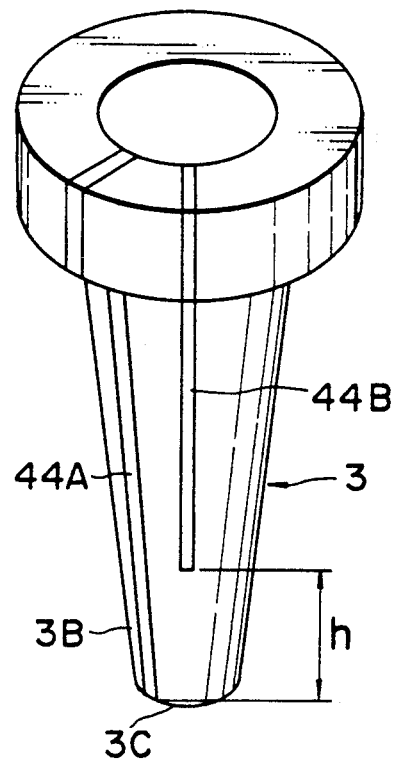
FIG. 9

DEVICE FOR ASPIRATING A FIXED QUANTITY OF LIQUID

BACKGROUND OF THE INVENTION

1. Field of the Invention

The present invention relates to a device for injecting a fixed quantity of liquid and more particularly, it relates to such device for use with automatic analysis machines for conducting bio-chemistry and blood type tests relating to bloods collected.

2. Description of the Related Art

When blood is to be transfused to a patient, biochemistry tests such as GOT and GPT, blood type tests according to ABO or Rh manner, screening to recognize irregular immune bodies in blood, tests to examine whether or not blood is infected with HBs, HBc, HIV and syphilis, and analysis of biocomponents such as α-fetoprotein and carcinoembryonic antigen which are present in an extremely fine amount in blood are conducted relating to bloods collected from other patients and blood suppliers.

In the case of the typical automatic analysis machine, these analyses are conducted in such a way that plural blood samples collected, particularly serum and blood-cells-floating liquid in the blood samples are successively injected into reaction trays by means of the liquid injection device and that reagents employed for each of the tests are injected into these reaction trays by means of the reagent injection device. The quantity of each of the blood samples to be injected must be exactly adjusted to enable the automatic analysis machine to conduct these analyses with high accuracy. Particularly in the case of analyzing α-fetoprotein and carcinoembryonic antigen in blood according to the immunological manner, or examining various kinds of infectious disease in blood, the carryover of blood must be eliminated in the course of successively injecting the blood samples into reaction trays.

In order to solve the above-mentioned problems, preliminarily-opened Japanese Patent Disclosure No. 62-247261 has proposed a liquid sucking device wherein the pipet to suck liquid sample can be disposed every time when the process of sucking the liquid sample is finished, the liquid sample is conveyed to that position where it does not reach the liquid sucking position and where its surface level is detected by a detector means, and the lowering of the pipet which is at the liquid sucking position is controlled responsive to a signal which is applied from the detector means and which represents the surface level of the liquid sample detected.

In the case of this liquid sucking device disclosed by the Japanese Patent Disclosure No. 62-247261, however, the surface level of liquid sample is detected at a position different from the liquid sucking position. This makes it necessary to drive the pipet at the liquid sucking position and also to drive the detector means at the surface level detecting position, thereby causing the device to become complicated in structure.

In the case where the detector means employed is of the electrode type, a means for cleaning the electrodes is needed to thereby make the device complicated in structure. In addition, the carryover of blood cannot be avoided in the course of cleaning the electrodes, thereby causing the accuracy of analyses to be reduced.

SUMMARY OF THE INVENTION

The object of the present invention is to provide a liquid injection device simple in construction and capable of detecting the surface level of liquid, and of injecting the liquid into a reaction tray without causing any carryover of the liquid.

This object of the present invention can be achieved by a liquid injection device comprising a means for sucking and injecting sample liquid and provided with a nozzle connecting portion; an injection nozzle attached to and detached from the nozzle connecting portion of said means; an electrode means arranged in the injection nozzle; conductive members arranged on the nozzle connecting portion of said sample liquid sucking and injection means and electrically connected to the electrode means in the injection nozzle when the nozzle is attached to the connecting portion; and a detector means connected to the conductor members to cooperate with the electrode means to detect the surface level of sample liquid.

According to the liquid injection device of the present invention, an electrode means for detecting the surface level of liquid is attached to the injection nozzle so that the surface level of the liquid to be sucked can be detected at the liquid sucking position. This makes the liquid injection device simpler in construction.

Further, the injection nozzle provided with the electrodes which serve to detect the surface level of the liquid, can be disposed of every time the process of sucking and injecting the liquid is finished. This can make cleaning unnecessary and prevent carryover of the liquid sample, thereby enabling the accuracy and reliability of analyses to be enhanced.

BRIEF DESCRIPTION OF THE DRAWINGS

FIGS. 7 and 8 show the process of manufacturing the second modification of the injection nozzle; and FIG. 9 is a perspective view showing a third modification of the injection nozzle.

DETAILED DESCRIPTION OF THE PREFERRED EMBODIMENTS

Some embodiments of the present invention will be described below with reference to the accompanying drawings.

Figure 1:
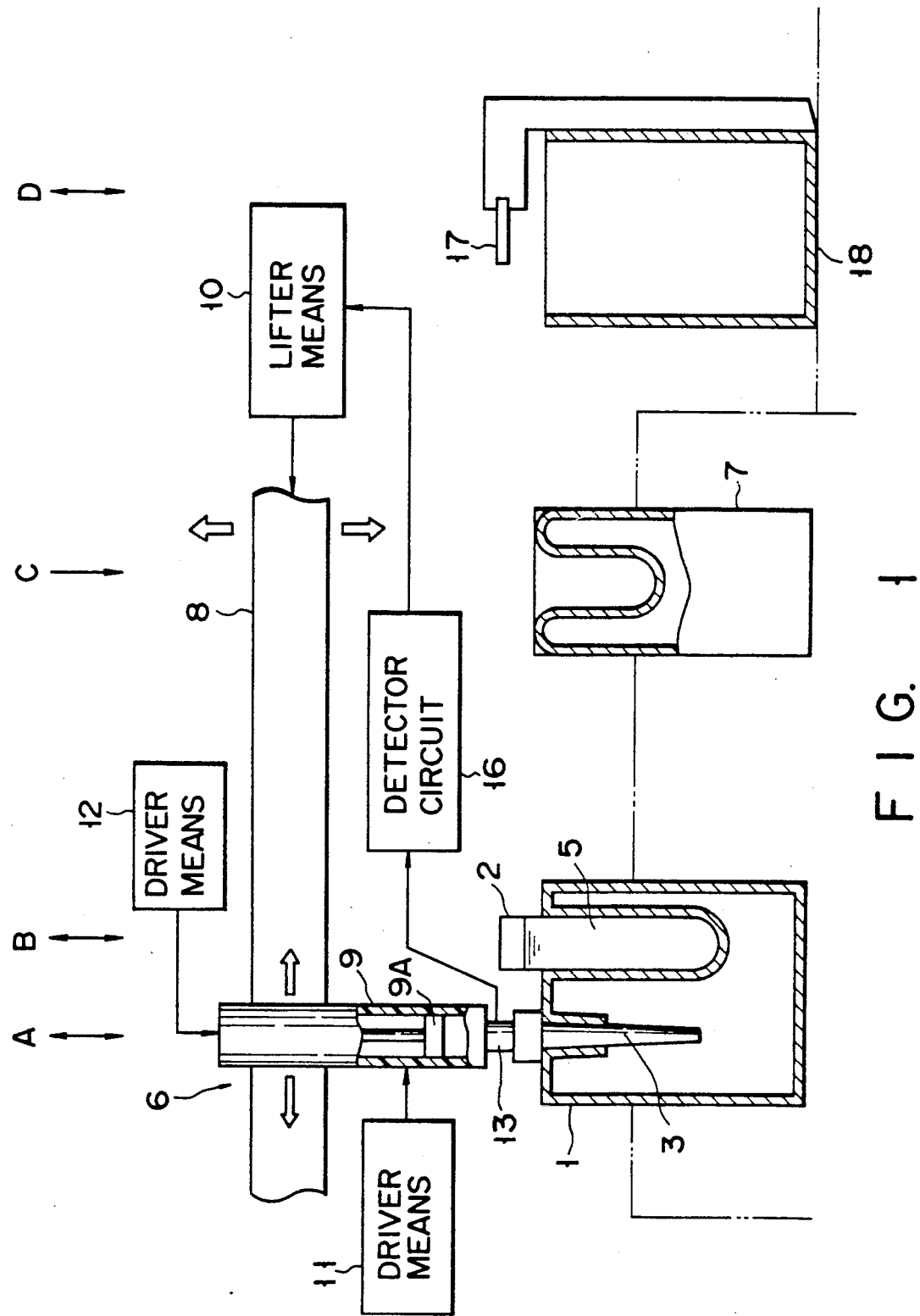
FIG. 1 is a side view showing a first embodiment of the liquid injection device according to the present invention, partly in section.
Figure 2:
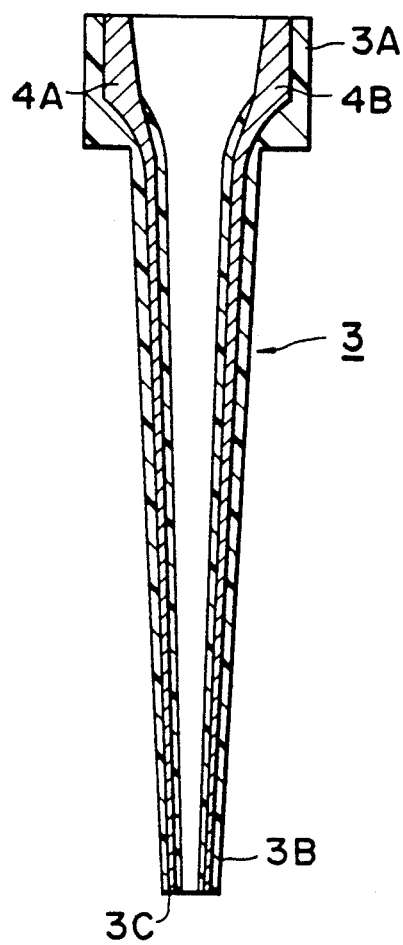
FIG. 2 is a vertically-sectioned enlarged view showing the injection nozzle in FIG. 1.

FIG. 1 shows a first example of the liquid injection device according to the present invention. Plural sample tubes 2 are arranged on sample rack 1 shown in FIG. 1 in a line and in a direction perpendicular to the sheet of paper on which FIG. 1 is drawn, while plural disposable injection nozzles 3 which correspond to their sample tubes 2 and which are detachable from sample rack 1, are also arranged on sample rack 1 at one side of sample tubes 2. As shown in section and on an enlarged scale in FIG. 2, each of injection nozzles 3 is made, hollow, of insulation resin such as ethylene tetrafluoride, having flange-like large-diameter base or upper portion 3A whose hollow is tapered as it comes nearer its lower end. A pair of line-like electrodes 4A and 4B each made of copper, iron, platinum or conductive resin are embedded in injection nozzle 3 along the axial direction thereof. These electrodes 4A and 4B are exposed from underside 3C of nozzle front or lower portion 3B as well as from the tapered inner wall of upper portion 3A.

In the case of this injection device according to the present invention, injection nozzle 3 is exchanged with a new one every time when it finishes processing its corresponding sample. Sample liquids 5 in sample tubes 2 on sample rack 1 are successively sucked and injected into dilution trays 7, respectively, by means of sucking and injection unit 6.

Unit 6 includes guide member 8 movable up and down and syringe 9 horizontally movable along guide member 8. The guide member 8 and syringe 9 are driven and controlled by lifter means and horizontally driver means 10 and 11. As schematically shown in FIG. 1, syringe 9 is moved to nozzle attaching position A, sample sucking position B, sample injecting position C and nozzle releasing position D by means of driver means 11, while guide member 8 is moved up and down by lifter means 10 after syringe 9 is moved to position A, B or D.

Figure 3:
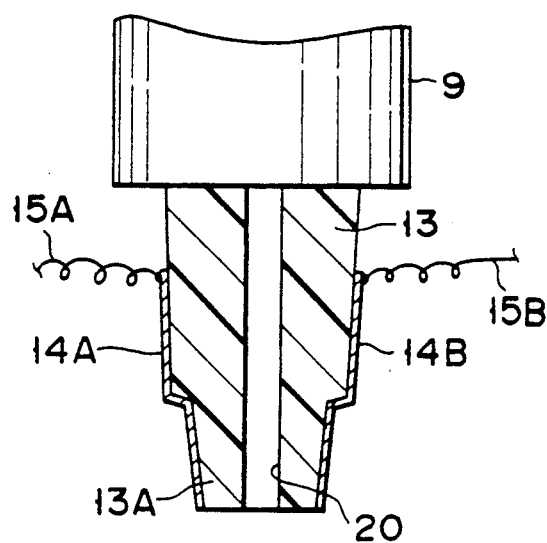
FIG. 3 is a vertically-sectioned enlarged view showing the nozzle connecting portion of the nozzle seat in FIG. 1.

Syringe 9 has piston 9A inside, which is driven and controlled by means 12. Syringe 9 has nozzle seat 13 at the front end thereof, to which injection nozzle 3 is attached. As shown in section and on an enlarged scale in FIG. 3, nozzle seat 13 is made, hollow, of insulation resin such as ethylene tetrafluoride, similarly to the case of injection nozzle 3, and through-hole 20 extending along the center axis of nozzle seat 13 is communicated with the hollow in syringe 9. Lower end portion 13A of nozzle seat 13 is tapered to reliably fit onto the tapered inner wall of upper portion 3A of injection nozzle 3. A pair of conductive members 14A and 14B each made of copper, iron, platinum or conductive resin are arranged on the outer wall of tapered lower end 13A of nozzle seat 13 and when nozzle seat 13 is fitted into injection nozzle 3, these conductive members 14A and 14B are connected to electrodes 4A and 4B exposed from the tapered inner wall of upper portion 3A of injection nozzle 3. Conductors 14A and 14B are also connected to circuit 16, which serves to detect the surface of sample liquid, via lead lines 15A and 15B, as shown in FIG. 1. Responsive to an output signal applied from liquid surface detector circuit 16, lifter means 10 is driven to adjust the lowering of guide member 8 or the entering of injection nozzle 3 into sample 5 when syringe 9 is at sample sucking position B.

Claw 17 for detaching injection nozzles 3 from nozzle seat 13 and container 18 for containing injection nozzles 3 detached from nozzle seat 13 are arranged at nozzle detaching or releasing position D. Claw 17 is engaged with flange-like upper portion 3A of injection nozzle 3, which has been fitted onto nozzle seat 13 of syringe 9, to release injection nozzle 3 from nozzle seat 13.

Syringe 9 is moved to nozzle attaching position A and then lowered to fit lower end portion 13A of nozzle seat 13 into upper portion 3A of injection nozzle 3, while contacting conductors 14A and 14B on the outer circumference of nozzle seat 13 with electrodes 4A and 4B of injection nozzle 3.

Syringe 9 is lifted, moved to sample sucking position B and then lowered. That length of injection nozzle 3 which is entered into sample liquid 5 is controlled as follows. The surface level of sample liquid 5 is detected by detector circuit 16, using underside 3C of injection nozzle 3, and underside 3C of injection nozzle 3 is then entered from the detected surface level into sample liquid 5 by a certain distance (or level) which equals the quantity of sample liquid 5 to be sucked. Holding injection nozzle 3 at this position, piston 9A is made operative causing injection nozzle 3 to suck the fixed quantity of sample liquid 5 into it.

Syringe 9 is then lifted and moved to sample injecting position C where piston 9A is operated to inject the fixed quantity of sample liquid 5 which has been sucked into injection nozzle 3, into dilution tray 7 through injection nozzle 3.

Syringe 9 is moved to nozzle releasing position D and then lowered by a certain distance (or level). Claw 17 is engaged with the top of flange-like upper portion 3A of injection nozzle 3 and syringe 9 is then lifted causing injection nozzle 3 to be released from nozzle seat 13 and dropped into container 18.

When one sample liquid is injected into dilution tray 7 as described above, sample rack 1 and the mount on which dilution trays 7 are mounted are moved by one pitch in the direction perpendicular to the sheet of paper on which FIG. 1 is drawn, and a next process of injecting another sample liquid into another dilution tray is started.

In the case of this injection device according to the present invention, therefore, an injection nozzle 3 is disposed of after every sample liquid and every sample liquid is injected into the dilution tray with a new injection nozzle 3.

Sample tubes 2 and injection nozzles 3 may be held not on the rack but on one or more turntables. Although injection nozzle 3 is attached to nozzle seat 13 at position A and detached from it at position D in the case of the first injection device, the attaching and detaching of each injection nozzle may be done at the same position (or position A, for example).

A second embodiment of the injection device according to the present invention will be described.

Figure 4:
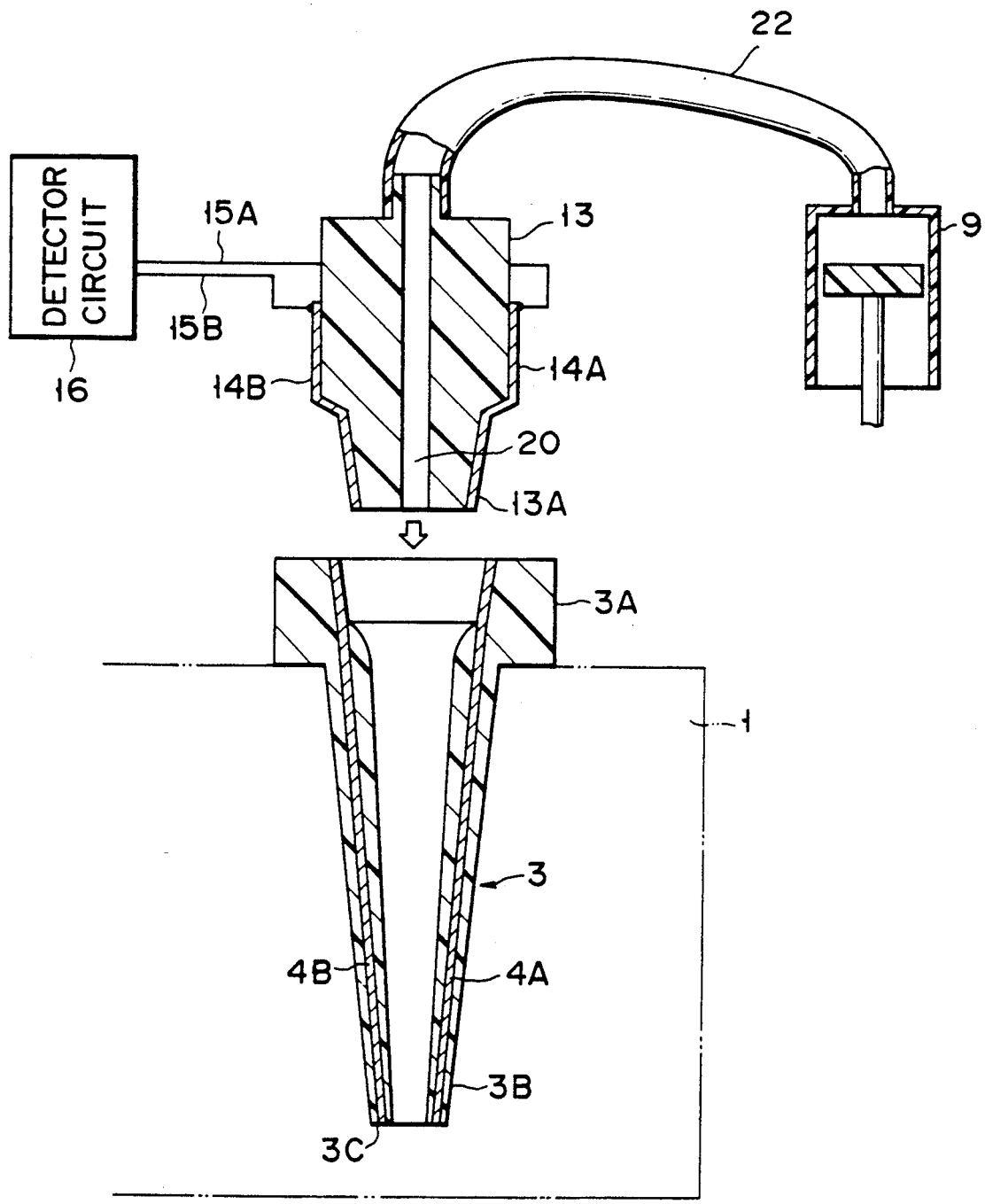
FIG. 4 is a side view showing a second embodiment of the liquid injection device according to the present invention partly in section.

As shown in FIG. 4, injection nozzle 3, similar to the one in the first injection device, is made, hollow, of insulation resin such as ethylene tetrafluoride and a pair of line-like electrodes 4A and 4B are embedded in injection nozzle 3 along the axial direction thereof. Each of paired electrodes 4A and 4B is made of copper, iron or platinum, for example. Base 3A of injection nozzle 3 is made like a flange having a large diameter and that portion of injection nozzle 3 which includes no base 3A but front portion 3B is tapered with a tapered hollow therein. Electrodes 4A and 4B are exposed from underside 3C as well as from the inner wall of base 3A of injection nozzle 3.

Injection nozzles 3 are held on sample rack 1, as shown in FIG. 4.

Nozzle seat 13 is made of insulation resin such as ethylene tetrafluoride as seen in the case of injection nozzle 3, and it has a through-hole 20 communicated with syringe 9. Front end 13A of nozzle seat 13 is tapered so as to fit onto the tapered inner wall of base 3A of injection nozzle 3. Conductors 14A and 14B made of copper, iron or platinum, for example, are arranged on the outer circumference of front end 13A and contacted with paired electrodes 4A and 4B exposed from the inner wall of base 3A of injection nozzle 3 when nozzle seat 13 is fitted into injection nozzle 3. Conductors 14A and 14B are also connected to detector circuit 16 through lead lines 15A and 15B.

This second injection device is different from the first one in that nozzle seat 13 is connected to syringe 9 through tube 22 and that only nozzle seat 13 is attached to the same driver means as those in the first injection device. Nozzle seat 13 and injection nozzle 3 are moved from nozzle attaching position A to sample sucking position B, sample injecting position C and nozzle releasing position D by means of the driver means.

Figure 5:
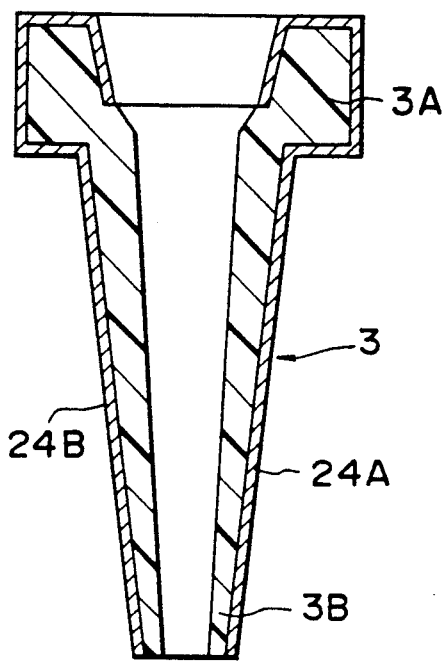
FIG. 5 is a vertically-sectioned view showing a first modification of the injection nozzle.

FIG. 5 shows a first modification of the injection nozzle. This injection nozzle 3 is made, hollow, of insulation resin such as ethylene tetrafluoride and both of the inner wall of base 3A and the outer circumference of front portion 3B of injection nozzle 3 are covered with a pair of strap-like conductors 24A and 24B each made of metal compound such as CdO and $SnO_2$.

Figure 6:
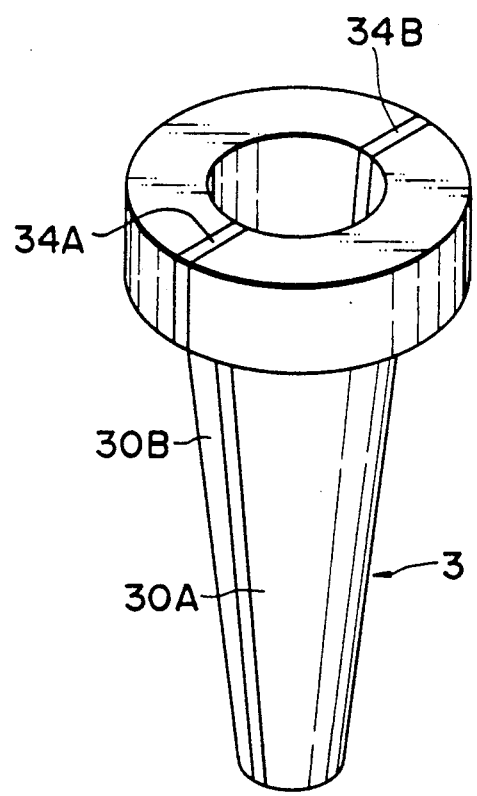
FIG. 6 is a perspective view showing a second modification of the injection nozzle.

FIGS. 6, 7 and 8 show a second modification of the injection nozzle. This injection nozzle 3 comprises conductive resin parts 34A and 34B made by mixing acrylic resin with conductive particles of copper or carbon, and insulation resin parts 30A and 30B made of ethylene tetrafluoride. Insulation resin parts 30A and 30B sandwich conductive resin parts 34A and 34B between them to form hollow injection nozzle 3. Conductive resin parts 34A and 34B serve as electrodes.

The process of manufacturing the second injection nozzle will be described. As shown in FIG. 7, halves 30A and 30B of injection nozzle 3 are made of insulation resin independently of the other and they are positioned in die 26 shown in FIG. 8, opposing to each other with a clearance interposed between them along a parting line. Conductive resin is then injected into the clearance between halves 30A and 30B of injection nozzle 3 in die 26 through injection nozzle 28 of the typical injection molding machine to form conductive resin parts 34A and 34B.

FIG. 9 shows a third modification of the injection nozzle. First conductor 44A arranged on the outer surface of injection nozzle 3 extends to underside 3C along the longitudinal direction of injection nozzle 3, but second conductor 44B terminates on the outer surface of injection nozzle 3, leaving distance (h) between its front end and underside 3C of injection nozzle 3. In other words, the front end of second conductor 44B is separated from that of first conductor 44A by distance (or height) (h) and this height (h) is determined depending upon a quantity of sample liquid to be sucked.

When the surface level of a sample is detected, lowering injection nozzle 3 at the sample sucking position and immersing conductors 44A and 44B on injection nozzle 3 into the sample liquid, injection nozzle 3 is fixed there and syringe 9 is made operative. This makes it easy to suck the predetermined quantity of sample liquid.

Conductors 44A and 44B have been arranged on the outer surface of injection nozzle 3 in the case of the third injection nozzle shown in FIG. 9, but they may be arranged on the inner surface of injection nozzle 3.

What is claimed is:

1. A device for injecting a fixed quantity of sample liquid, comprising:
   syringe means for aspirating and injecting a liquid sample, including a nozzle connecting portion;
   an injection nozzle made of insulation resin and detachably connected to said nozzle connecting portion of said syringe means;
   electrode means arranged in said injection nozzle and including a pair of conductive lines embedded in the injection nozzle;
   conductive members arranged on the nozzle connecting portion of said syringe means, and positioned so as to be electrically connected to the electrode means in the injection nozzle when the nozzle is attached to the nozzle connecting portion of the syringe means; and
   detector means electrically connected to said conductive members for operation in association with said electrode means, for detecting a surface level of the sample liquid while the injection nozzle is attached to said nozzle connecting portion wherein said injection nozzle has an upper end and a lower end, one of said conductive lines extending from said lower end to said upper end of the injection nozzle, and the other of said conductive lines terminating at a point which is a certain distance or height away from said lower end of said injection nozzle, wherein said distance or height corresponds to a fixed quantity of sample liquid to be aspirated through the injection nozzle.

2. A device for injecting a fixed quantity of sample liquid, comprising:
   syringe means for aspirating and injecting a sample liquid, including a nozzle connecting portion;
   an injection nozzle made of insulation resin and detachably connected to said nozzle connecting portion of said syringe means;
   electrode means arranged in said injection nozzle and including a pair of first conductive members coated on the outer surface of the injection nozzle;
   second conductive members arranged on the nozzle connecting portion of said syringe means, and positioned so as to be electrically connected to the first conductive members of the electrode means in the injection nozzle when the nozzle is attached to the nozzle connecting portion of the syringe means; and
   detector means electrically connected to said second conductive members for operation in association with said electrode means, for detecting a surface level of the sample liquid while the injection nozzle is attached to said nozzle connecting portion wherein said injection nozzle has an upper end and a lower end, one of said first conductive members extending from said lower end to said upper end of the injection nozzle, and the other of said first conductive members terminating at a point which is a certain distance or height away from said lower end of said injection nozzle, wherein said distance or height corresponds to a fixed quantity of sample liquid to be aspirated through the injection nozzle.

3. A device for injecting a fixed quantity of sample liquid, comprising:
   syringe means for aspirating and injecting a sample liquid, including a nozzle connecting portion;
   an injection nozzle detachably connected to said nozzle connecting portion of said syringe means, said nozzle including parts made of conductive resin and parts made of insulation resin;
   conductive members arranged on the nozzle connecting portion of said syringe means, and positioned so as to be electrically connected to the conductive resin parts in the injection nozzle when the nozzle is attached to the nozzle connecting portion of the syringe means; and detector means electrically connected to said conductive members for operation in association with said conductive resin parts of said injection nozzle, for detecting a surface level of the sample liquid while the injection nozzle is attached to the nozzle connecting portion of said syringe means wherein said injection nozzle has an upper end and a lower end, and said conductive resin parts form a pair of electrodes extending from said upper end of said injection nozzle, one of said electrodes extending from said upper end to said lower end of the injection nozzle, and the other of said electrodes terminating at a point which is a certain distance or height away from said lower end of said injection nozzle, wherein said distance or height corresponds to a fixed quantity of sample liquid to be aspirated through the injection nozzle.

4. A disposable injection nozzle for preventing contamination and for use with a liquid injection device provided with detector means for detecting the surface level of a sample liquid, comprising:

a nozzle body formed so as to be detachably connectable to the liquid injection device; and electrode means attached to the nozzle body and positioned so as to be electrically connected with the detector means when the nozzle body is connected to the liquid injection device, and to detect the surface level of sample liquid to be aspirated for enabling the detector means to provide an output signal to the liquid injection device when the nozzle body is at a sample liquid aspirating position, said nozzle body having upper and lower ends and said electrode means including a pair of electrodes extended from said upper end, one of said pair of electrodes extending from the upper end to the lower end of the nozzle body while the other of said pair of electrodes terminates part of the way toward the lower end of the nozzle body, leaving a distance or height between said other of said pair of electrodes and said lower end of the nozzle body, said distance or height corresponding to a fixed quantity of sample liquid to be aspirated.

5. The injection nozzle according to claim 4, wherein said nozzle body includes parts made of conductive resin and parts made of insulation resin, and said parts made of conductive resin also forming said electrode means.

6. The injection nozzle according to claim 4, wherein said nozzle body is made of insulation resin.

7. The injection nozzle according to claim 6, wherein said electrode means comprises conductive lines embedded in the nozzle body.

8. The injection nozzle according to claim 6, wherein said electrode means comprises conductive members coated on an outer surface of the nozzle body.

* * * * *